US011906354B2

(12) United States Patent
Frach et al.

(10) Patent No.: US 11,906,354 B2
(45) Date of Patent: Feb. 20, 2024

(54) RECHARGE CIRCUIT FOR DIGITAL SILICON PHOTOMULTIPLIERS

(71) Applicant: AVAGO TECHNOLOGIES INTERNATIONAL SALES PTE. LIMITED, Singapore (SG)

(72) Inventors: Thomas Frach, Aachen (DE); Torsten Solf, Aachen (DE)

(73) Assignee: AVAGO TECHNOLOGIES INTERNATIONAL SALES PTE. LIMITED, Singapore (SG)

( * ) Notice: Subject to any disclaimer, the term of this patent is extended or adjusted under 35 U.S.C. 154(b) by 156 days.

(21) Appl. No.: 17/626,464

(22) PCT Filed: Jul. 16, 2020

(86) PCT No.: PCT/EP2020/070115
§ 371 (c)(1),
(2) Date: Jan. 11, 2022

(87) PCT Pub. No.: WO2021/013681
PCT Pub. Date: Jan. 28, 2021

(65) Prior Publication Data
US 2022/0283025 A1 Sep. 8, 2022

Related U.S. Application Data

(60) Provisional application No. 62/876,260, filed on Jul. 19, 2019.

(51) Int. Cl.
*G01J 1/44* (2006.01)
*A61B 6/03* (2006.01)

(52) U.S. Cl.
CPC .............. *G01J 1/44* (2013.01); *A61B 6/037* (2013.01); *G01J 2001/442* (2013.01); *G01J 2001/4466* (2013.01)

(58) Field of Classification Search
CPC ... G01J 1/44; A61B 6/03; G01T 1/248; G01S 7/48
(Continued)

(56) References Cited

U.S. PATENT DOCUMENTS 9,268,033 B2    2/2016  Frach
11,340,109 B2*  5/2022  Hennecke ............ G01S 7/4863
(Continued)

FOREIGN PATENT DOCUMENTS

CN    107024286 A    8/2017
CN    108681362 A    10/2018

OTHER PUBLICATIONS

International Search Report and Written Opinion of PCT/EP2020/070115, dated Oct. 15, 2020.
(Continued)

*Primary Examiner* — Que Tan Le
(74) *Attorney, Agent, or Firm* — Foley & Lardner LLP

(57) ABSTRACT

The present application relates generally to silicon photomultiplier (SiPM) detector arrays. In one aspect, there is a system including an array of cells each including a single-photon avalanche diode (SPAD) reverse-biased above a breakdown voltage of the SPAD. Each cell may further include trigger logic connected to the SPAD, and configured to output a trigger signal indicating whether the SPAD is in breakdown. Each cell may still further include a conditional recharge circuit configured to recharge the SPAD conditional upon both (i) the recharge circuit applying the recharge signal to the cell and (ii) the trigger signal output by the trigger logic of the cell indicating the SPAD of the cell is in breakdown.

20 Claims, 6 Drawing Sheets

(58) Field of Classification Search
USPC .......................................... 250/214 R, 214.1
See application file for complete search history.

(56) References Cited

U.S. PATENT DOCUMENTS

| | | |
|---|---|---|
| 2008/0290259 A1 | 11/2008 | Mathewson |
| 2011/0079727 A1 | 4/2011 | Prescher |
| 2016/0011321 A1 | 1/2016 | Solf |
| 2016/0182902 A1 | 6/2016 | Guo |
| 2018/0106911 A1 | 4/2018 | Jackson |
| 2018/0195900 A1 | 7/2018 | Delic |

OTHER PUBLICATIONS

Field, Ryan M. et al. "A 100 fps, Time-Correlated Single-Photon-Counting-Based Fluorescence-Lifetime Imager in 130 nm CMOS", IEEE Journal of Solid-State Circuits, vol. 49, No. 4, Apr. 2014.

Vornicu, I. et al "A CMOS 8x8 SPAD Array for Time-of-Flight Measurement and Light-Spot Statistics", Circuits and Systems (ISCAS), 2013 IEEE International Symposium, 2013.

Nolet et al Quenching Circuit and SPAD Integrated in CMOS 65 nm with 7.8 ps FWHM Single Photon Timing Resolution, Instruments, 2018.

Frach et al, "The Digital Silicon Photomuliplier Principle of Operation and Intrinsic Detector Performance", IEEE Nuclear Science Symposium Conference. 2009.

\* cited by examiner

RECHARGE CIRCUIT FOR DIGITAL SILICON PHOTOMULTIPLIERS

CROSS-REFERENCE TO PRIOR APPLICATIONS

This application is the U.S. National Phase application under 35 U.S.C. § 371 of International Application No. PCT/EP2020/070115, filed on Jul. 16, 2020, which claims the benefit of U.S. Provisional Patent Application No. 62/876,260, filed on Jul. 19, 2019. These applications are hereby incorporated by reference herein.

BACKGROUND

The following relates to silicon photomultiplier (SiPM) detector arrays of the type often used in digital Positron Emission Tomography (PET) systems, astronomy detectors, Light Detection and Ranging (LIDAR) systems, and the like. In a SiPM used for digital PET, each pixel of the detector array is itself composed of an array of cells, with each cell including a single photon avalanche diode (SPAD) that is reverse biased above its breakdown voltage, and a portion of the supporting circuitry. The supporting circuitry includes sub-modules for generating and validating a trigger event when a SPAD goes into breakdown, and counting the breakdown events across the array of cells of the pixel for a time interval after the trigger event. Following the trigger event (e.g. after breakdown), quench and refresh circuitry are used for accelerating reinstatement of a SPAD. Some illustrative examples of SiPM detector arrays for PET are described in Frach et al., U.S. Pat. No. 9,268,033 titled "Digital Silicon Photomultiplier for TOF-PET", and Solf, U.S. Pub. No. 2016/0011321 A1 titled "Timestamping Detected Radiation Quanta".

The following discloses certain improvements that addresses these problems and others.

SUMMARY

In one disclosed aspect, an optical detector comprises: an array of cells; and a recharge circuit configured to apply a recharge signal to groups of cells of the array. In some embodiments, each cell includes: a single-photon avalanche diode (SPAD) reverse-biased above a breakdown voltage of the SPAD; trigger logic connected to the SPAD, and configured to output a trigger signal indicating whether the SPAD is in breakdown; and a conditional recharge circuit configured to recharge the SPAD conditional upon both (i) the recharge circuit applying the recharge signal to the cell and (ii) the trigger signal output by the trigger logic of the cell indicating the SPAD of the cell is in breakdown.

In another disclosed aspect, a method comprises: with trigger logic connected to a single-photon avalanche diode (SPAD), outputting a trigger signal indicating that the SPAD is in breakdown. The method may further include, with a conditional recharge circuit: receiving the trigger signal indicating that the SPAD is in breakdown; receiving a recharge signal indicating to recharge the SPAD; in response to receiving the trigger signal indicating that the SPAD is in breakdown and receiving a recharge signal indicating to recharge the SPAD, recharging the SPAD.

In another disclosed aspect, an optical detector comprises: an array of cells each including: a single-photon avalanche diode (SPAD) reverse-biased above a breakdown voltage of the SPAD; and trigger logic connected to an anode of the SPAD, and configured to output a trigger signal. In some embodiments, each cell of the array is configured to connect the SPAD to a ground when a recharge signal is applied, and the recharge signal comprises a duty cycle.

One advantage resides in preventing a "domino effect" breakdown of SPADs if a dark count happens during recharge.

Another advantage resides in an improved recharge circuit.

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION

However, certain problems can arise due to noise. Specifically, a so-called dark count is a SPAD breakdown that is not related to a photon detection, but mostly due to thermally generated carriers in the single-photon avalanche diode junction. Such dark counts can lead to false triggers thereby introducing undesirable detector deadtime as the false trigger is processed, rejected, and the SiPM reset. Furthermore, if a breakdown occurs during recharge, a breakdown domino effect can occur in which neighboring SPADS also breakdown.

The following relates to silicon photomultiplier (SiPM) detector arrays of the type often used in medical nuclear imaging systems such as digital Positron Emission Tomography (PET) systems. However, there are many applications of the disclosed approaches both inside and outside of the field of nuclear medical imaging.

Figure 1:
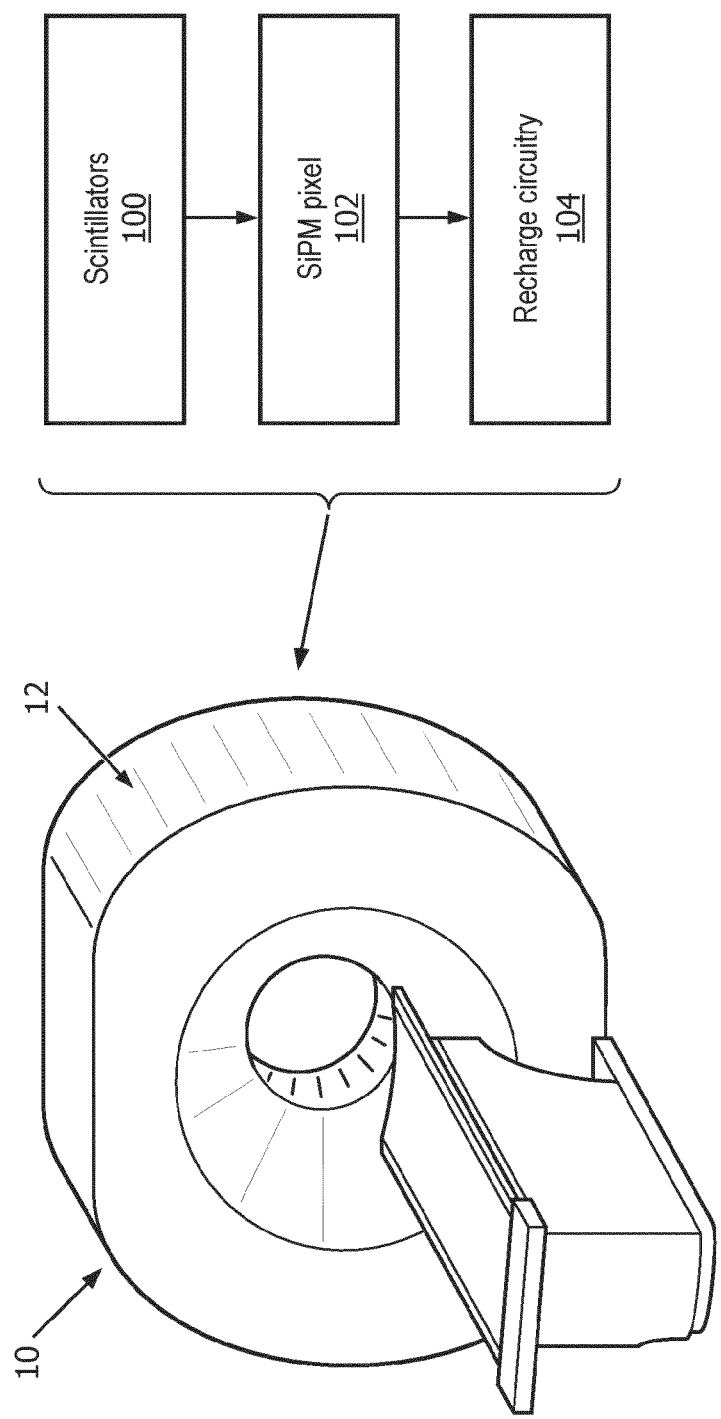
FIG. 1 diagrammatically illustrates an embodiment of a PET scanning system.

With reference to FIG. 1, a radioemission imaging system 10 includes scanner 12. The scanner 12 is arranged and sized to receive a prone human subject in an examination region.

Different scanning techniques and variations may be used in medical nuclear imaging. One such technique is PET. In one example of PET, a subject is administered a radiopharmaceutical that includes a positron-emitting radioisotope. The radiopharmaceutical may be designed to aggregate in an organ or tissue of interest, such as the brain, lungs, a tumor, or so forth. After administration of the radiopharmaceutical, the subject is loaded into the examination region. As time progresses, the radiopharmaceutical will emit positrons in radioactive decay events. A positron emitted by the radiopharmaceutical will travel for a short (generally negligible) distance before interacting with an electron. Once the positron interacts with the electron, both the positron and the electron will be annihilated and a pair of oppositely directed gamma photons (sometimes also called annihilation photons) are produced. The gamma photons move in opposite directions and each may be detected upon reaching a scintillator 100 in scanner 12. This example may depend on simultaneous detection of the pair of gamma photons. Therefore, some algorithms may discount gamma photons that do not arrive simultaneously.

To detect the gamma photons, silicon photomultiplier (SiPM) detector arrays are used. In these detectors, each pixel of the detector array is itself composed of an array of cells, with each cell including a single photon avalanche diode (SPAD) reverse biased above its breakdown voltage, and a portion of the supporting circuitry. (In the following, the term "pixel" is used to refer to the array of SPAD cells, since in PET applications this array of cells forms one pixel of the larger PET detector array. However, it will be appreciated that in some other applications, a single array of SPAD cells may be employed, e.g. as a radiation detector in a LIDAR system, in which case there may be only a single "pixel".) The supporting circuitry includes sub-modules for generating and validating a trigger event when a SPAD goes into breakdown, counting the breakdown events across the array of cells of the pixel for a time interval after the trigger event, and assigning a digital timestamp to the event. Quench and refresh circuitry are used after breakdown for accelerating reinstatement of a SPAD. To provide high spatial resolution in a PET detector design, the silicon real estate occupied by each cell is made as small as practicable. While some supporting circuitry must be in the area of the cell in the array, where feasible parts of the supporting circuitry are placed at the periphery of the pixel, and are also designed to service multiple cells (e.g. an entire row of cells). Some illustrative examples of SiPM detector arrays for PET are described in Frach et al., U.S. Pat. No. 9,268,033 titled "Digital Silicon Photomultiplier for TOF-PET", and Solf, U.S. Pub. No. 2016/0011321 A1 titled "Timestamping Detected Radiation Quanta", both of which are incorporated herein by reference in their entireties.

The complete PET radiation detector for detecting gamma rays further includes scintillators 100 that generate a flash of light (scintillation) when a gamma ray is absorbed. The SiPM pixel 102 detects the burst of photons that make up the scintillation. The total number of counts over an integration time interval is a metric of the photon energy of the detection event, while the timing of the trigger signal provides the timestamp for the event. Furthermore, it is desirable to operate the SiPM at room temperature, or at least to limit the amount of cooling.

Of interest here, the recharge circuitry 104 is located at the periphery of the pixel area, and a single recharge circuit is connected with a row of cells of the pixel. In its quiescent state, the SPAD is biased a few volts above its breakdown voltage. When the SPAD breaks down, the voltage over the junction decreases below its breakdown voltage, and must be brought back up above the breakdown voltage to reset the SPAD. The recharge circuit operates by briefly turning on a transistor to connect the anode of the SPAD to ground, thereby putting electrical charge onto the anode and bringing the broken down SPAD above its breakdown voltage so as to return to the quiescent state.

Furthermore, the active quench and recharge circuits minimize the dead time of the SPADs. Ideally, these circuits would be designed to quench and recharge each SPAD individually (see Nolet at al., "Quenching Circuit and SPAD Integrated in CMOS 65 nm with 7.8 ps FWHM Single Photon Timing Resolution," Instruments, 2018). However, the circuitry required for individual SPAD quench and recharge is typically large and may require analog components for adjust the quench and recharge timings. Therefore, providing an individual recharge circuit for each SPAD cell may not be practical, especially in an application such as a PET detector in which high spatial resolution is desired, which drives toward making the SPAD cells as small as practicable.

Alternatively, common row recharge technique can be used to reduce the area requirements and to off-load the timing circuitry to the periphery of the sensor (see Frach et al., "The Digital Silicon Photomultiplier— Principle of Operation and Intrinsic Detector Performance," in IEEE Nuclear Science Symposium conference record. Nuclear Science Symposium, December 2009). In this case, each SPAD is quenched independently but multiple SPADs (typically one or more rows) are recharged at once. This method significantly reduces the area of the cell electronics and leads to higher photon detection efficiency of the device due to higher fill factor.

Figure 2:
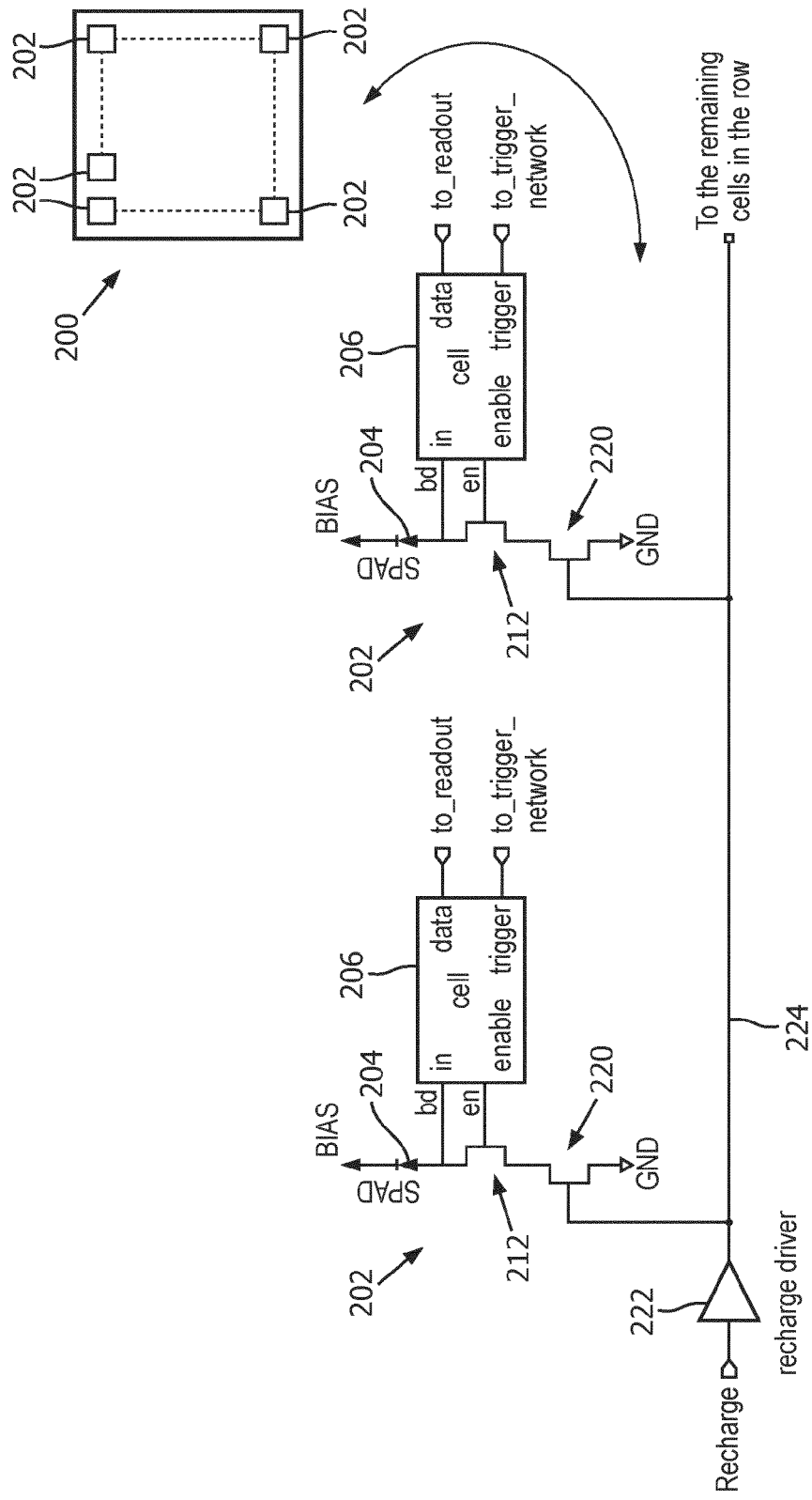
FIG. 2 illustrates an example of common row recharge.

FIG. 2 illustrates an example of an electrical schematic of two cells of a row of cells in a SPAD, which have common row recharge. With reference thereto, each cell 202 includes a single-photon avalanche diode (SPAD) (204) reverse-biased above a breakdown voltage of the SPAD, and trigger logic 206 connected to the SPAD 204. The trigger logic 206 is configured to output a trigger signal to a trigger network of the pixel indicating whether the SPAD 204 is in breakdown. The illustrative trigger logic 206 performs additional functionality that includes generating a readout signal on a readout line, and controlling an optional enabling transistor 212 that can be used to disconnect the SPAD 204 (e.g., if the SPAD 204 is defective and should be deactivated). Some illustrative examples of suitable trigger logic are disclosed in Frach et al., U.S. Pat. No. 9,268,033 and Solf, U.S. Pub. No. 2016/0011321 A1.

As further seen in FIG. 2, each cell 202 further includes a recharge transistor 220 that controls recharging of the SPAD 204. The recharge transistors 220 of the cells 202 are part of a recharge circuit that is configured to apply a recharge signal to rows of cells of the array. (More generally, the recharge circuit is configured to apply a recharge signal to groups of cells of the array; in the illustrative example the groups are rows of cells of the array, but other groupings are contemplated). The recharge circuitry further includes a recharge driver 222 for each row that outputs the recharge signal, and an electrical conductor 224 connecting the driver 222 to the recharge transistors 220 of all cells of the row. In this way, the driver 222 outputting the recharge signal applies the recharge signal to the recharge transistors 220 of all cells of the row. In operation, the pixel controller detects the occurrence of a SPAD breakdown anywhere on the row (e.g., via the readout and/or trigger signals output by the trigger logic 206) and controls the driver 222 to output the recharge signal. In the illustrative examples, the recharge signal is an active-high signal (i.e. logical "1") signal, so that the driver 222 outputs a low signal (logical "0") until the pixel controller activates the driver 222 to output the active-high recharge signal. (It is contemplated to employ the reverse arrangement, in which the recharge signal is active-low, as will be discussed below). The active-high recharge signal applied to the gate of the recharge transistor 220 of each cell 202 causes the anode of the SPAD 204 to be connected to electrical ground, thereby putting electrical charge onto the anode and bringing the broken down SPAD above its breakdown voltage so as to return to the quiescent state.

Embodiments employing the "reverse arrangement", in which the recharge signal is active-low are also contemplated. In these embodiments, the recharge transistor is of the PMOS type (the illustrated recharge transistor 220 in FIG. 2 is NMOS, as it is open when the gate is logic 0 and closed when logic 1) and also the entire circuit is "inverted". By way of background, U.S. Patent Application Publication No. 2011/0079727 A1 illustrates some aspects of both ways of readout.

To further illustrate, in embodiments disclosed herein, the SPAD is tied to GND when the recharge transistor is closed. With positive bias (=Vbreakdown+Vexcess) at the cathode, the SPAD is biased at Vexcess above the breakdown voltage when the recharge NMOS opens. When the SPAD breaks down, current flows in the junction until the anode-cathode voltage drops to Vbreakdown. As the cathode potential is fixed, only the anode potential can change and so the anode voltage increases from GND to ~Vexcess (assuming the NMOS transistor is open, otherwise large current will flow through the SPAD).

For the PMOS embodiment, the recharge transistor is connected to the cathode in order to connect to the supply defining the excess voltage. In this case, the anode is biased at negative Vbreakdown and the PMOS recharge connects the cathode to the supply rail defining Vexcess. The cathode of the SPAD stays at Vexcess when the recharge switch opens and the cathode voltage transitions to GND on breakdown. The entire logic of the cell circuit that follows is thus inverted.

An advantage of this common row recharge design is that the only component of the recharge circuit that needs to be located locally within the cell 202 is the recharge transistor 220. The recharge driver 222 can be located at the periphery of the array 200 of cells 202. This facilitates miniaturization of the cells 202 thereby enabling smaller pixels and a PET detector having higher spatial resolution. Alternatively, the pixel size may be kept fixed, and the disclosed approach enables increasing the fill factor of the cell (that is, reduce the fractional area of the cell that is insensitive to light) and thereby increase the sensitivity of the sensor. Higher sensitivity leads to better timing resolution of the sensor (and system). It will be noted that when any cell in the row breaks down, the recharge driver is activated by the pixel controller to apply the recharge signal to the entire row (or other group) of cells that includes the cell in breakdown. However, connecting the anode of a SPAD that is in its quiescent state (i.e. reverse-biased above its breakdown voltage) to electrical ground via its recharge transistor 220 does not change the state of the SPAD, because it merely slightly increases the magnitude of the reverse bias further above its breakdown voltage. Hence, the common row recharge design is typically understood to provide advantageous reduction in the total number of parts and consequent miniaturization of the array 200, without concomitant cost.

As noted, with the common row recharge design, the recharge circuit brings the anodes of all SPADs of the entire row to ground, regardless of whether any particular SPAD in the row has broken down. Ordinarily this is not a problem, as the SPADs that are not currently broken down will remain in their quiescent state. However, it is recognized herein that if such a SPAD in its quiescent state (that is, biased above the breakdown voltage and not in breakdown), and with its anode connected to electrical ground via its recharge transistor 220, happens to undergo breakdown then the pn junction of the SPAD flows a large electrical current and the SPAD effectively becomes a photoemitter. The light emitted by the SPAD can then trigger breakdown in neighboring SPADs (breakdown domino effect).

In other words, one problem of the common row recharge circuit occurs when a SPAD breaks down during the recharge cycle for the row containing that SPAD. In some SiPM designs for PET detector pixels, there are several tens of SPADs connected to the recharge line 224, and not all SPADs are discharged when the recharge starts. Accordingly, there is a realistic chance that one of the SPADs that is in its quiescent state subsequently breaks down after its recharge transistor 220 is closed. In this case, a large electrical current starts to flow through the SPAD, thereby leading to high photoemission. This photoemission subsequently triggers breakdowns in neighboring SPADs in the same line or in other line (breakdown domino effect). This state ends with the end of the recharge, and leads to a spurious event with sometimes several thousands of photons being emitted by the initial SPAD causing many other SPADs to break down. This combined "domino effect" produces some events that pass the energy-based validation threshold creating "noise" events, thus increasing deadtime of the sensor. A fraction of these events also fall within the energy window of the system, thus increasing the random coincidence rate of the PET imaging system.

The systems and methods disclosed herein implement two solutions for this problem: one solution employing additional circuitry, and the other solution employing a modification of the signal applied on the recharge line. It should be understood that the two solutions can be used in combination with one another, or separately. Some embodiments of the first solution include an additional circuit located in the area of the cell; the additional circuit performs a logical AND of the recharge line and the trigger line (with some buffering involved) and applies the output of the logical AND to the transistor ordinarily activated by the recharge line alone. More generally, the additional circuit gates the recharge line by the trigger line. Hence, the SPAD anode is only brought to ground if both: (i) the recharge line is active, and (ii) the particular SPAD has been triggered (and hence is in breakdown). On the other hand, a SPAD that is in its quiescent state will have a logical "0" on its (buffered) trigger line, so that its anode will not be brought to ground.

In other words, the recharge pulse is applied only to SPADs that are discharged. While this does not change the probability of SPAD breakdowns, it eliminates the large current flowing through the SPAD undergoing breakdown and thereby significantly reduces the likelihood of the breakdown domino effect. Moreover, the circuit is compact thereby facilitating miniaturization of the cells, and reduces the load of the row recharge line, thereby leading to faster recharge times and lower power consumption of the row recharge line driver.

Figure 3:
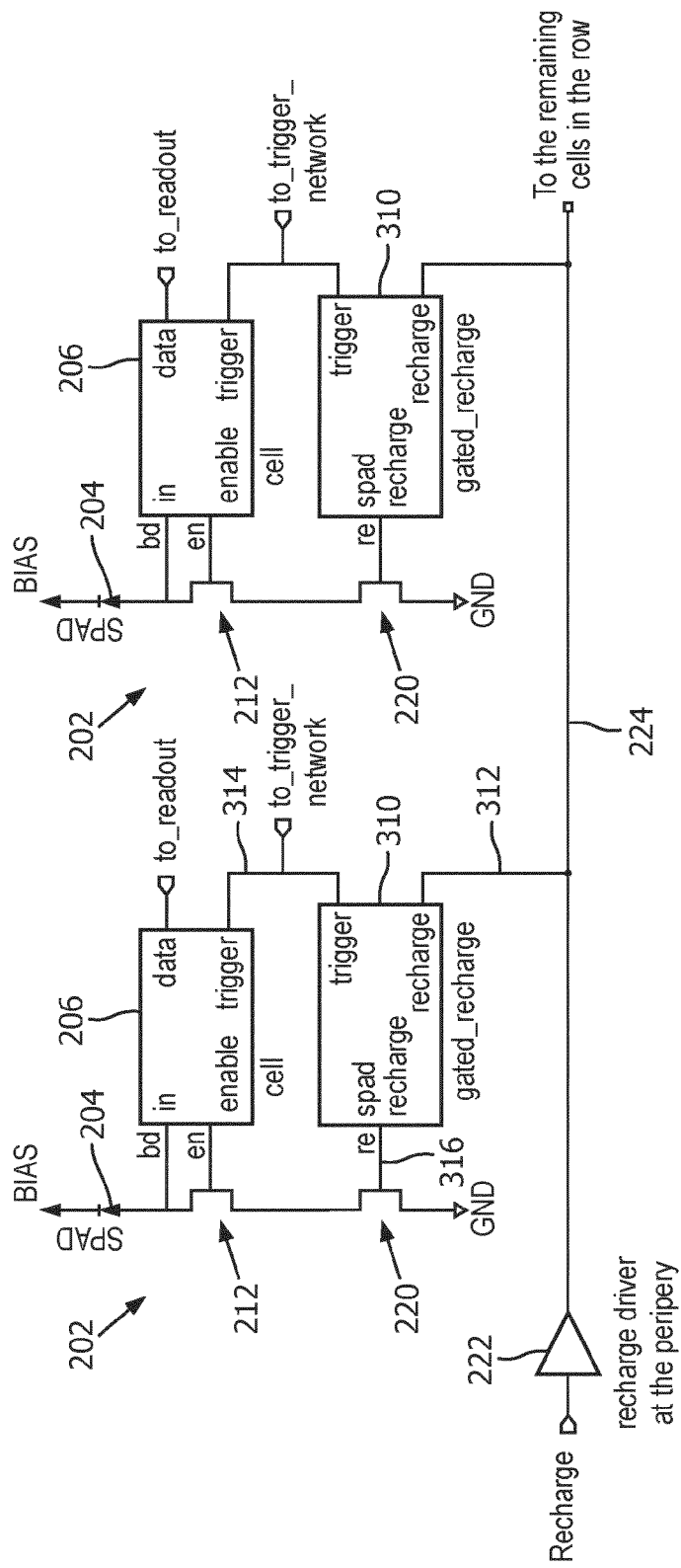
FIG. 3 illustrates an embodiment of cell including an exemplary conditional recharge circuit to form a configuration of row recharge with gated recharge.

FIG. 3 illustrates an example of an electrical schematic of two cells of a row of cells in a SPAD, which have common row recharge including an additional circuit 310 that, together with the recharge transistor 220 already described with reference to FIG. 2, forms a conditional recharge circuit 220, 310 that is configured by the additional circuit 310 to recharge the SPAD 204 conditional upon both (i) the recharge circuit 222, 224 applying the recharge signal to a row of cells that includes the cell and (ii) the trigger logic 206 of the cell indicating the SPAD 204 of the cell is in breakdown. As seen in FIG. 3, the additional circuit 310 receives as input the recharge signal 312 via the conductor 224, and also receives as a second input the trigger signal 314 that is output by the trigger logic 206 and indicates whether the SPAD 204 of the cell is in breakdown. The additional circuit 310 outputs a gated recharge signal 316 which is the recharge signal 312 gated by the trigger signal 314.

In the illustrative example, the recharge signal 312 is active-high (i.e. logic "1" operates to recharge the SPAD 204 via the recharge transistor 220) and the trigger signal is also active-high (i.e. logic "1" indicates the SPAD 204 is in breakdown, logic "0" indicates it is not in breakdown). For this case, the additional circuit 310 operates as a logical AND gate, implementing the logic:

gated recharge signal (316)=recharge signal (312) AND trigger signal (314)

so that the gated recharge signal 316 is only logical "1" if both the recharge signal 312 is logical "1" and the trigger signal is logical "1". It will be appreciated that the logic implemented by the additional circuit may be different if different active states are employed. For example, if the recharge signal is active-high but the trigger signal is active-low (i.e. logic "0" indicates the SPAD is in breakdown) then the additional circuit suitably implements the logic: gated recharge signal=recharge signal (312) AND NOT trigger signal.

Figure 4:
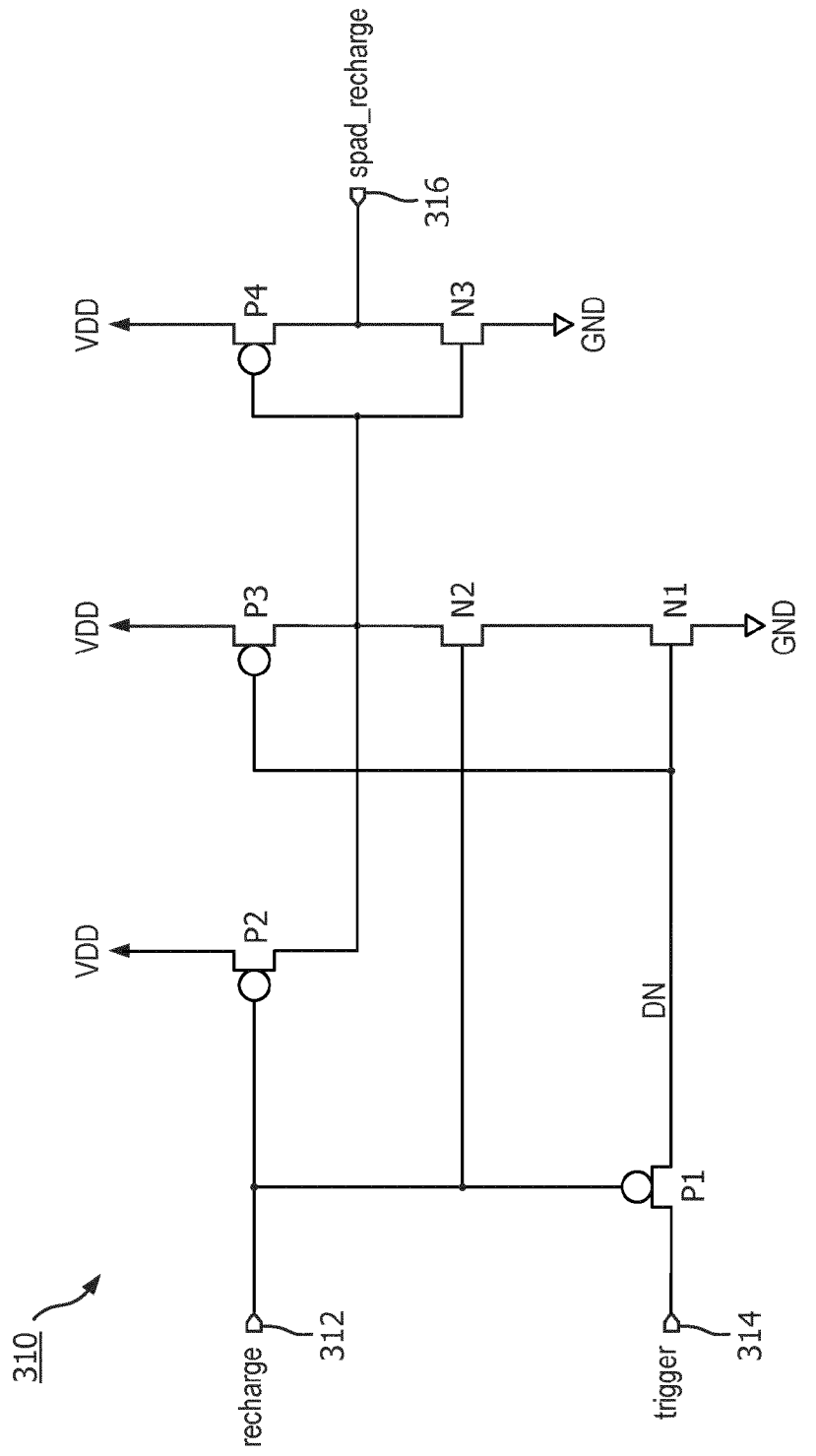
FIG. 4 shows an example conditional recharge circuit.

FIG. 4 shows an example implementation of the additional circuit 310. The additional circuit 310 is implemented in each cell 202 (as shown in FIG. 3) and therefore should be compact in order to maintain a high fill factor for the cell for high photon detection efficiency. The basic function of the illustrative example of FIG. 4 is as follows: the recharge pulse 312 stores dynamically the state of the trigger 314 output of the cell on the node DN. The recharge signal 312 is active-high, thereby opening the p-channel field-effect transistor (P-FET) P1 connecting the trigger signal 314 to DN for the time of the recharge. The remaining transistors implement a logical AND function between the state stored on node DN and the recharge signal 312, i.e. spad recharge=recharge AND DN.

To further illustrate background on DN, the state of the SPAD is to be stored at the beginning of the recharge pulse for the time of the recharge, otherwise the recharge of the SPAD would stop shortly after the anode reaching the threshold voltage of the attached logic (~Vexcess/2). By storing the status on DN, it is ensured that the recharge transistor of the SPAD is closed for full time of the recharge.

The dynamic storage (the state is stored on the gate capacitance of N1 and P3) has the advantage of small area and high speed; however, it has only limited storage time due to leakage. The PMOS P1 is one-half of a transmission gate. The NMOS is omitted here to save area, but could be easily added by adding an NMOS controlled by the inverted recharge signal (additional NMOS+inverter NMOS/PMOS needed). Other storage elements (latches, flipflops) could be used as well at the cost of silicon area.

Advantageously, the additional circuit 310 of FIG. 4 includes only seven transistors, and accordingly can be made compact.

The second solution is to add a duty cycle to the recharge line. In some embodiments, the duty cycle is added as part of a pulse train of the recharge line 224. As shown by experiments reported herein (see FIGS. 5 and 6 and related text) this approach is also very effective for suppressing the breakdown domino effect, and can be used alone or in combination with the additional circuit of the first solution.

The physical reason that the second solution works is that when a breakdown occurs during the short recharge pulse, the SPAD gets a chance to recover during the OFF state. The recharge pulse width and duty cycle can be made adjustable (e.g. 10 ns, 50%). The duration of the ON state is suitably chosen based on the time it takes the recharge transistor to charge the SPAD capacitance to Vexcess, typically few nanoseconds. The duration of the off-state depends on the time it takes the SPAD to remove the charge from the junction and to discharge any traps in the bandgap (otherwise leading to afterpulsing). This part also depends on the operating temperature, as the trap lifetime is a function of temperature.

Figure 5:
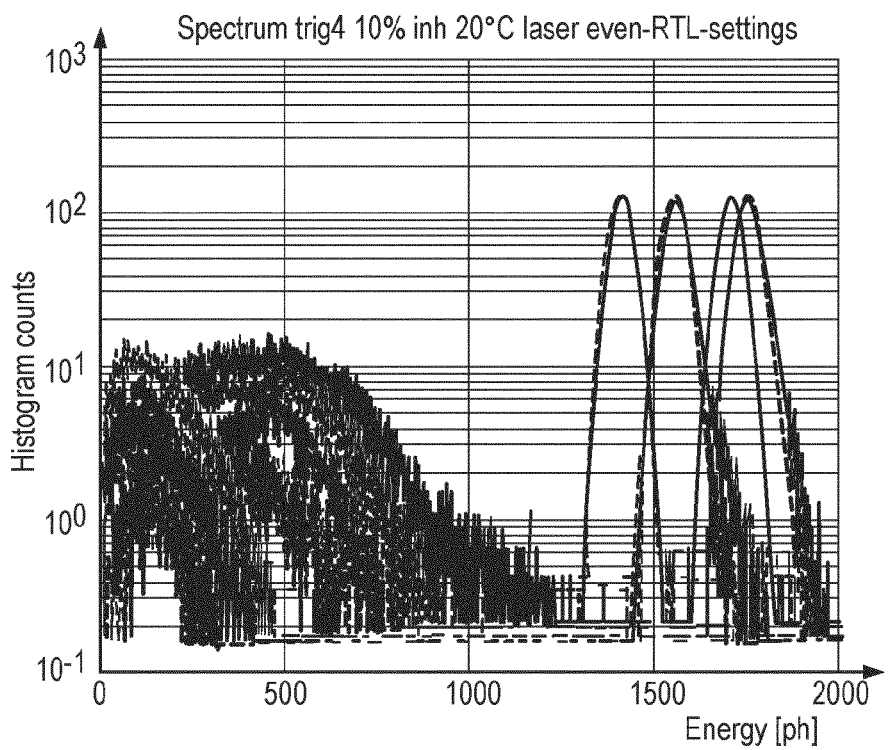
FIG. 5 illustrates an example of data of a conventional recharge.
Figure 6:
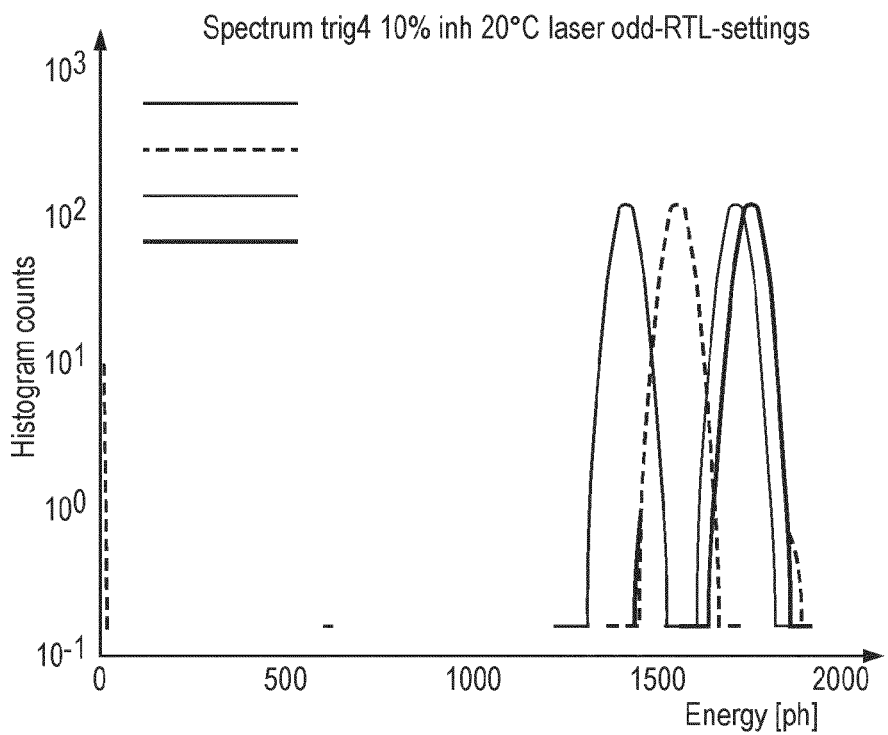
FIG. 6 illustrates an example of data of a smart recharge with 50% duty cycle.

To further explain the second solution, further suppression of the photoemission and domino effect can be achieved by adding a duty cycle to the recharge pulse. A recharge pulse of typically 10 ns length with 50% duty cycle has proven very effective in suppressing the photoemission, as shown in FIGS. 5 and 6 which report experimental results for four sensor pixels. FIG. 5 shows data obtained using static recharge pulse of 10 ns length and the circuit of FIG. 2 (without the additional circuit (310)). The data shown in FIG. 5 exhibits noise events over a broad energy range of up to 1000 ph (i.e., the unit "ph" indicates photon count, i.e. 1000 ph indicates a detected noise "event" with time-integrated energy of 1000 photons) in addition to the desired signal of photopeak events in the energy range of 1500 ph-2000 ph. By contrast, FIG. 6 shows data using 10 ns recharge pulse with 50% duty cycle and the circuit of FIG. 3 (with the additional circuit (310)). As seen in FIG. 6, the noise events in the range 0-1000 ph are virtually eliminated.

For the data shown in FIGS. 5 and 6, photopeak events were generated by a diffuse laser illumination with a total energy of 1500 ph-2000 ph (depending on the location of the four sensor pixels). The dark count rate of the SPAD matrix is generated by thermal noise at 20° C.

More particularly, it can be seen that in the case of the circuit of FIG. 2 and without pulsing the recharge signal (i.e., 100% "duty cycle"), common row recharge leads to low energy noise events (FIG. 5) with energies of several hundred photons. In contrast, as illustrated in FIG. 6, with the additional circuit (310) and using a duty cycle of 50%, the noise events are removed almost completely. As shown by a comparison of FIGS. 5 and 6, the disclosed improved recharge efficiently removes the probability of correlated SPAD breakdown during the recharge phase.

Figure 7:
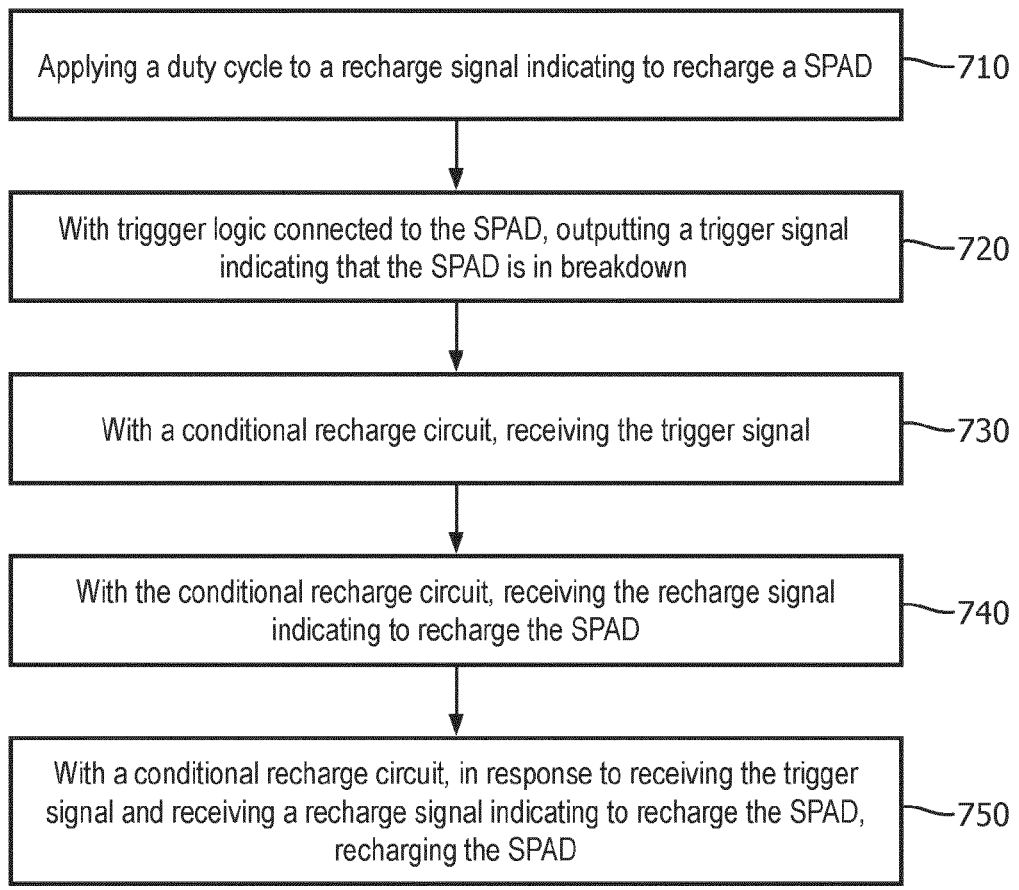
FIG. 7 diagrammatically illustrates a flowchart of an embodiment in accordance with the systems and methods described herein.

FIG. 7 diagrammatically illustrates a flowchart of an embodiment in accordance with the systems and methods described herein. At step 710 a duty cycle is applied to a recharge signal indicating to recharge a SPAD. At step 720, with trigger logic connected to the SPAD, a trigger signal indicating that the SPAD is in breakdown is outputted. At step 730, with a conditional recharge circuit, the trigger signal is received. At step 740, with the conditional recharge circuit, the recharge signal indicating to recharge the SPAD is received. At step 750 with the conditional recharge circuit, in response to receiving the trigger signal and receiving a recharge signal indicating to recharge the SPAD, the SPAD is recharged.

In addition to PET, there are many other applications of the disclosed techniques, especially when used at high temperatures (due to increased SPAD breakdowns at higher temperatures). More generally, other applications which require detection of optical pulses with high temporal resolution timestamping are contemplated. Other applications include, for example, PET/CT, PET/MR, SPECT, high energy physics, LIDAR, and fluorescence-lifetime imaging microscopy. Of particular interest is LIDAR systems which perform optical ranging based on time-of-flight between emission of a laser beam and detection of its reflection. LIDAR finds application in diverse industries including automotive, where it is used, for example, as a triggering device for activating emergency braking.

It will be further appreciated that the techniques disclosed herein may be embodied by a non-transitory storage medium storing instructions readable and executable by an electronic data processing device to perform the disclosed techniques. Such a non-transitory storage medium may comprise a hard drive or other magnetic storage medium, an optical disk or other optical storage medium, a cloud-based storage medium such as a RAID disk array, flash memory or other non-volatile electronic storage medium, or so forth.

The invention has been described with reference to the preferred embodiments. Modifications and alterations may occur to others upon reading and understanding the preceding detailed description. It is intended that the exemplary embodiment be construed as including all such modifications and alterations insofar as they come within the scope of the appended claims or the equivalents thereof.

The invention claimed is:

1. An optical detector, comprising:
an array of cells; and
a recharge circuit configured to apply a recharge signal to groups of cells of the array;
wherein each cell includes:
 a single-photon avalanche diode (SPAD) reverse-biased above a breakdown voltage of the SPAD;
 trigger logic connected to the SPAD, and configured to output a trigger signal indicating whether the SPAD is in breakdown; and
 a conditional recharge circuit configured to recharge the SPAD conditional upon both (i) the recharge circuit applying the recharge signal to the cell and (ii) the trigger signal output by the trigger logic of the cell indicating the SPAD of the cell is in breakdown.

2. The optical detector of claim 1 wherein:
the groups of cells of the array are rows of cells of the array; and
the recharge circuit for each row includes a recharge driver for outputting the recharge signal and an electrical conductor connecting the output of the recharge driver to the conditional recharge circuits of all cells of the row.

3. The optical detector of claim 1 wherein the conditional recharge circuit is configured to recharge the SPAD by bringing the anode of the SPAD to electrical ground.

4. The optical detector of claim 1 wherein:
the cells each further include a p-channel field-effect transistor (P-FET) (P1);
the recharge signal is connected to a gate of the P-FET (P1); and
the trigger signal is connected to a source of the first P-FET (P1).

5. The optical detector of claim 1 wherein:
the recharge signal is connected to: a gate of a first p-channel field-effect transistor (P-FET) (P1), a gate of a second P-FET (P2), and a gate of a n-channel field-effect transistor (N-FET) (N1); and the trigger signal is connected to a source of the P-FET (P1).

6. The optical detector of claim 1 wherein the recharge signal comprises a pulse train with a duty cycle.

7. The optical detector of claim 1 wherein the recharge signal has a variable pulse width.

8. The optical detector of claim 6 wherein the recharge signal comprises 10 ns pulses.

9. The optical detector of claim 6 wherein the duty cycle is 50%.

10. A method comprising:
with trigger logic connected to a single-photon avalanche diode (SPAD), outputting a trigger signal indicating that the SPAD is in breakdown; and
with a conditional recharge circuit:
 receiving the trigger signal indicating that the SPAD is in breakdown;
 receiving a recharge signal indicating to recharge the SPAD;
 in response to receiving the trigger signal indicating that the SPAD is in breakdown and receiving a recharge signal indicating to recharge the SPAD, recharging the SPAD.

11. The method of claim 10 wherein the conditional recharge circuit recharges the SPAD by bringing the anode of the SPAD to a ground.

12. The method of claim 10 wherein:
the recharge signal is sent to a gate of a P-FET (P1); and
the trigger signal is sent to a source of the P-FET (P1).

13. The method of claim 10 wherein:
the recharge signal is sent to: a gate of a first p-channel field-effect transistor (P-FET) (P1), a gate of a second P-FET (P2), and a gate of a n-channel field-effect transistor (N-FET) (N1); and
the trigger signal is sent to a source of the first P-FET (P1).

14. The method of claim 10 wherein the recharge signal comprises a pulse train with a duty cycle.

15. The method of claim 14 wherein the recharge signal comprises 10 ns pulses.

16. The method of claim 15 wherein the duty cycle is 50%.

17. An optical detector, comprising:
an array of cells each including:
 a single-photon avalanche diode (SPAD) reverse-biased above a breakdown voltage of the SPAD; and
 trigger logic connected to an anode of the SPAD, and configured to output a trigger signal;
wherein each cell of the array is configured to connect the SPAD to a ground when a recharge signal is applied, and wherein the recharge signal comprises a pulse train with a duty cycle.

18. The optical detector of claim 17 wherein the recharge signal comprises 10 ns pulses.

19. The optical detector of claim 17 wherein the duty cycle is 50%.

20. The optical detector of claim 17 wherein at least one of the duty cycle and a cycle length of the pulse train is configurable.

* * * * *